United States Patent
Anderskewitz et al.

[11] Patent Number: 6,037,377
[45] Date of Patent: Mar. 14, 2000

[54] AMIDINE DERIVATIVES, THE PREPARATION AND USE THEREOF AS MEDICAMENTS WITH LTB4 ANTAGONISTIC EFFECT

[75] Inventors: Ralf Anderskewitz, Bingerbruck; Kurt Schromm; Ernst-Otto Renth, both of Ingelheim; Frank Himmelsbach, Mittelbiberach; Franz Birke, Ingelheim; Armin Fugner, Gau-Algesheim, all of Germany

[73] Assignee: Boehringer Ingelheim KG, Ingelheim, Germany

[21] Appl. No.: 08/460,961

[22] Filed: Jun. 5, 1995

Related U.S. Application Data

[63] Continuation of application No. 08/352,003, Dec. 8, 1994, abandoned, which is a continuation of application No. 08/129,154, Nov. 22, 1993, abandoned.

[30] Foreign Application Priority Data

Feb. 5, 1992 [DE] Germany ............... 42 03 201
Jul. 23, 1992 [DE] Germany ............... 42 24 289
Dec. 24, 1992 [DE] Germany ............... 42 44 241

[51] Int. Cl.$^7$ ............... A61K 31/155; C07C 257/18
[52] U.S. Cl. ............... 514/635; 564/247; 564/300; 564/86; 514/351; 514/470; 514/546; 514/603; 549/401; 549/462
[58] Field of Search ............... 564/225, 229, 564/247; 549/401, 437; 514/456, 469, 631, 637

[56] References Cited

FOREIGN PATENT DOCUMENTS

| | | |
|---|---|---|
| 292977 | 11/1988 | European Pat. Off. . |
| 366066 | 5/1990 | European Pat. Off. . |
| 518818 | 12/1992 | European Pat. Off. . |
| 518819 | 12/1992 | European Pat. Off. . |

OTHER PUBLICATIONS

March Advanced Organic Chemistry, 3rd Edition, pp. 342, 344 and 359 (1985).
B. R. Baker et al, Journal of Medicinal Chemistry, vol. 12, 1969, pp. 408–414.
Crowin Hansch et al, Journal of Medicinal Chemistry, vol. 17, 1974, pp. 1160–116.

*Primary Examiner*—Richard L. Raymond
*Attorney, Agent, or Firm*—R.P. Raymond; M-E. M. Devlin; A. Stempel

[57] ABSTRACT

Compounds of the formula (I)

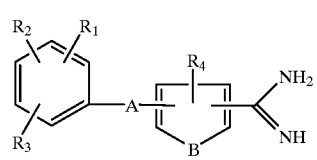

which is explained more fully in the specification, may be prepared by conventional methods and used therapeutically in conventional galenic preparations.

6 Claims, No Drawings

AMIDINE DERIVATIVES, THE PREPARATION AND USE THEREOF AS MEDICAMENTS WITH LTB4 ANTAGONISTIC EFFECT

This is a continuation of application Ser. No. 08/352,003, filed Dec. 8, 1994, now abandoned which is a continuation of application Ser. No. 08/129,154, filed Nov. 22, 1993, now abandoned.

The invention relates to new amidine derivatives, the preparation thereof using conventional methods and their use in pharmaceutical compositions.

The new amidine derivatives correspond to the formula

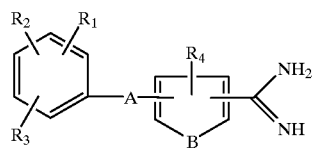

(I)

wherein $R_1$ and $R_2$, which may be identical or different, denote $CF_3$, halogen, $R_5$, $OR_5$, $COR_6$, $SR_6$, $SOR_6$, $SO_2R_6$, $SO_2NR_5R_7$, $C(OH)R_5R_7$ or together may also denote the double-bonded groups $-CR_8=CR_9-CH=CH-$, $-CH=CR_8-CR_9=CH-$, $-CR_8=CH-CR_9=CH-$, $-O-CHR_{10}-CH_2-$, $-O-CH_2-O-$, $-O-CH_2-CH_2-O-$, $-(CH_2)_{3-4}-$, $-NH-CO-O-$, $-NH-CO-CH_2-O-$, $-CO-CH_2-O-$ or $-CO-CH_2-CH_2-O-$, linked with adjacent carbon atoms of the benzene ring, whilst these groups may in turn be substituted by $C_{1-4}$-alkyl, $R_3$ denotes halogen, OH, $CF_3$, $R_5$, $OR_6$, $COR_6$, $CONHR_5R_7$, $CH_2OH$, $CH_2-O-(C_{1-4}$-alkyl), $SR_6$, $SOR_6$, $SO_2R_6$, $SO_2NR_5R_7$, $NH-CO-(C_{1-4}$-alkyl), $NH-SO_2-(C_{1-4}$-alkyl), $NR_5R_7$ or $C(OH)R_5R_7$ (whilst if $R_3$ is the same as $R_5$, $R_5$ can only denote H if at least one of the substituents $R_1$ and $R_2$ does not denote H), a heterocyclic 5-membered ring having 1 to 3 heteroatoms and of the formula

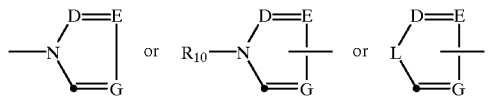

(wherein D, E and G, which may be identical or different, denote CH, N, C—($C_{1-4}$-alkyl) or C-phenyl and L denotes O or S), $R_4$ denotes halogen, $NH_2$, NH—($C_{1-4}$-alkyl), N($C_{1-4}$-alkyl)$_2$, OH, $C_{1-4}$-alkoxy, $R_5$ denotes H, $C_{1-12}$-alkyl, phenyl, phenyl optionally substituted by halogen, $C_{1-4}$-alkyl, $C_{1-4}$-alkoxy or $C_{2-5}$-acyl, or phenyl-($C_{1-4}$-alkyl), $R_6$ denotes $C_{1-12}$-alkyl, phenyl, or phenyl optionally substituted by halogen, $C_{1-4}$-alkyl, $C_{1-4}$-alkoxy or $C_2$–$C_5$-acyl, $R_7$ denotes H or $C_{1-12}$-alkyl, $R_8$, $R_9$ (which may be identical or different) denote H, OH, $C_{1-4}$-alkyl, $C_{1-4}$-alkoxy or $C_{2-5}$-acyl, $R_{10}$ denotes H or $C_{1-4}$-alkyl, $R_{11}$, $R_{12}$, which may be identical or different, denote H, OH, halogen, $CF_3$, $C_{1-4}$-alkyl or $C_{1-4}$-alkoxy, A denotes one of the groups $X_1-A_1-X_2$ (II)

$X_2-A_2-X_3$ (III)

$X_4-A_2-X_2$ (IV)

$(CH_2)_{1-2}-NH-CO-(CH_2)_{1-3}-X_2$ (V)

$-CH=CH-A_2X_2$ (VI)

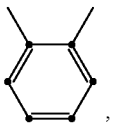

(VII)

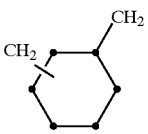

(VIII)

B denotes CH=CH, CH=N, S or

$A_1$ denotes $C_{2-4}$-alkylene, cis- or trans-$CH_2-CH=CH-CH_2$, $CH_2-C\equiv C-CH_2$ or

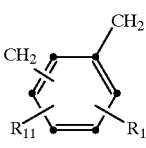

(IX)

(IXa)

(IXb)

$A_2$ denotes $C_{1-5}$- alkylene, $X_1$ denotes O, NH, S, SO, $SO_2$, CO, $CH_2$ or

$X_2$ denotes O, NH, S or

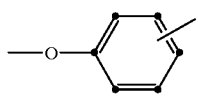

denotes NH—CO, CO—NH, SO$_2$—NH or

$X_4$ denotes NH—CO, CO—NH, NH—SO$_2$, SO$_2$—NH or NH—CO—NH, and (if they contain one or more chiral centres), may occur in the form of racemates, in enantiomerically pure or concentrated form, possibly as pairs of diastereomers and (if a double bond is present) in cis- or trans-form and as free bases or as salts, preferably with physiologically acceptable acids.

Within the scope of the above definitions, the preferred compounds are the compounds of formula

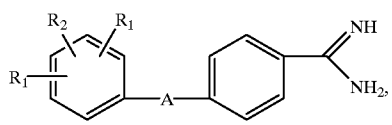

(I')

wherein $R_1$, $R_2$, which may be identical or different, denote $R_7$, $OR_7$, $COR_6$, halogen or together denote the double bonded groups —CR$_8$=R$_9$—CH=CH—, —CH=CR$_8$—CR$_9$=CH—, —O—CHR$_{10}$—CH$_2$— or —CO—CH$_2$—CH$_2$—O—, linked with adjacent carbon atoms of the benzene ring, $R_3$ denotes halogen, CF$_3$, $R_7$, $OR_7$, CO—(C$_{1-4}$-alkyl), NH—CO—(C$_{1-4}$-alkyl), NHSO$_2$—(C$_{1-4}$-alkyl) or N(R$_{10}$)$_2$ (whilst $R_7$ can only denote H if at least one of the substituents $R_1$ and $R_2$ does not denote H) or a heterocyclic five-membered ring such as

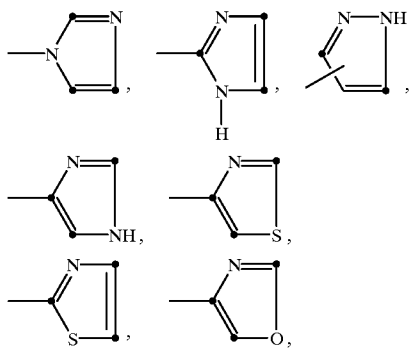

$R_6$ and $R_7$ are as hereinbefore defined, and

A denotes the group II.

The following may be particularly mentioned as examples of the group of formula —C$_6$H$_2$R$_1$R$_2$R$_3$:

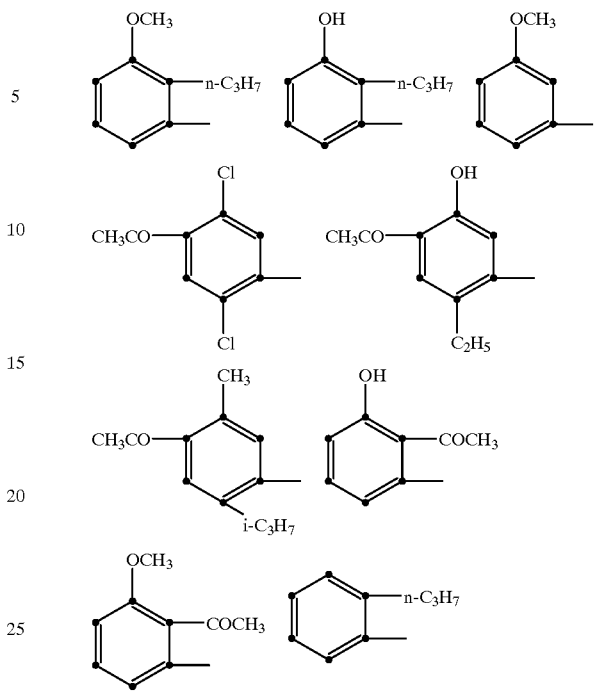

of the definitions of A particular mention may be made of:

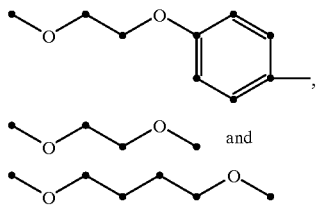

Special mention should also be made of the compounds of formula

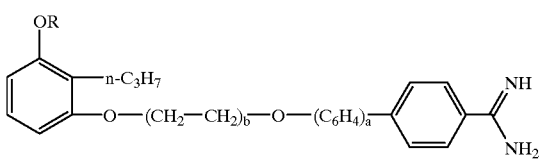

wherein a denotes 0 or 1, b denotes 1 or 2,

R denotes C$_{1-4}$-alkyl, and if a=0 or 1 and b=1, and if a=1 and b=2, R may also denote hydrogen, and R preferably denotes CH$_3$, C$_2$H$_5$ or H, and for a=1, b is preferably 1.

In the above definitions, the term halogen denotes F, Cl, Br or I, preferably F, Cl. If the groups listed are alkyl chains or contain alkyl chains, these may be straight-chained or branched. The alkyl chains in $R_5$, $R_6$ and $R_7$ preferably contain up to 6 carbon atoms, more particularly 1 to 4 carbon atoms. In particular, as a constituent of COR$_6$, R$_6$ denoting alkyl may also be mono- or poly-fluorine-substituted. Particular examples of substituents of ring systems are alkyls such as methyl, ethyl and the propyl. A preferred acyl group is COCH$_3$, a preferred alkoxy group is CH$_3$O. The bridge A preferably contains 4 to 6 members. The group is arranged between the two ring systems in formula I and in corresponding formulae so as to correspond to the written form of formulae II to VI, whereas the groups which are valid for both R$_1$ and R$_2$ are not listed in the proper orientation. If R$_1$ and R$_2$ together denote a double bonded group, R$_3$ preferably denotes H or C$_{2-5}$-acyl, e.g. acetyl. The groups R$_1$, R$_2$ and R$_3$ should not all simultaneously denote CF$_3$, COR$_6$, SR$_6$, SOR$_6$, SO$_2$R$_6$, SO$_2$NR$_5$R$_7$ or C(OH)R$_5$R$_7$, but rather these groups as well as OR$_5$, with the definition phenoxy or substituted phenoxy, preferably occur only once or possibly twice, whilst alkyl, acyl and halogen, in particular, may occur as further substituents. The bonds or CH$_2$ groups in IX/IXa/IXb are generally in the α-position to one another. Typical groups for A are, for example, O—(CH$_2$)$_2$—O, O—(CH$_2$)$_4$—O, whilst one of the O-atoms may be replaced by S, NH or Co, as well as groups such as CH$_2$—CH$_2$—CONH, CH$_2$—CH$_2$—NH—CO, CO—NH—CH$_2$—CH$_2$ or NH—CO—CH$_2$—CH$_2$. The amidino group is usually in the para-position relative to the carbon atom to which A is linked.

The new compounds are prepared by conventional methods.

1. Reaction of imidoesters of the formula

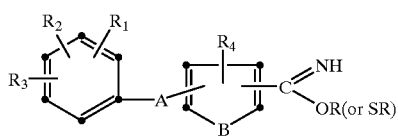

(X)

wherein R$_1$ to R$_4$, A and B are as hereinbefore defined and R preferably represents a C$_{1-6}$-alkyl group or benzyl (but if desired the man skilled in the art can also use derivatives of other alcohols), and ammonia. The reaction is preferably carried out in an organic solvent at temperatures between about 0° C. and the boiling temperature of the reaction mixture, preferably between ambient temperature and about 100° C. or the boiling temperature, if this is lower. Suitable solvents are polar solvents such as methanol, ethanol and propanol.

If the starting materials are sufficiently acid-resistant the reaction may be carried out via the corresponding acid imide chlorides instead of the imidoesters.

2. In order to prepare compounds of formula I wherein A is linked via O or S to at least one of the ring systems:

Reaction (a) of a phenol or thiophenol of formula

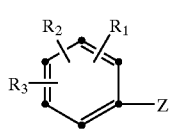

(XI)

wherein Z denotes OH or SH and R$_1$, R$_2$ and R$_3$ are as hereinbefore defined, with a compound of the formula

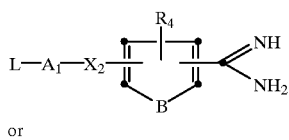

(XII)

or

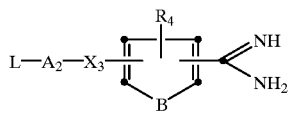

(XIII)

wherein A$_1$, A$_2$, B, R$_4$, X$_2$ and X$_3$ are as hereinbefore defined and L represents a nucleofugic leaving group, or (b) of a phenol or thiophenol of the formula

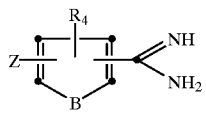

(XIV)

wherein B, R$_4$ and Z are as hereinbefore defined, with a compound of the formula

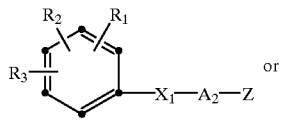

(XV)

or

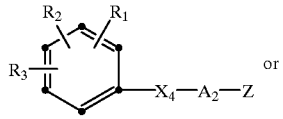

(XVI)

or

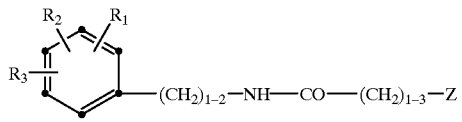

(XVII)

or

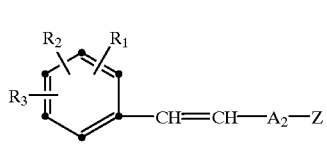

(XVIII)

wherein A$_1$, A$_2$, R$_1$, R$_2$, R$_3$ and Z are as hereinbefore defined.

The reaction is carried out in aprotic solvents such as dimethylsulphoxide, dimethylformamide, acetonitrile or alcohols such as methanol, ethanol or propanol with the addition of a base (metal carbonates, metal hydroxides, metal hydrides) at temperatures between about 0 and 140° C. or the boiling temperature of the reaction mixture.

The phenols or thiophenols may also be used in the form of salts, e.g. alkali metal salts. Examples of suitable nucleofugic leaving groups include halogens such as Br and Cl.

3. Reduction of an amidoxime of the formula

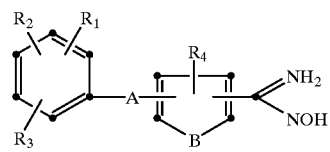

(XIX)

wherein A, B and $R_1$ to $R_4$ are as hereinbefore defined.

For the reduction of XIX it is appropriate to use catalytic hydrogenation, particularly with Raney nickel in a lower alcohol such as methanol. Conveniently, the amidoxime of formula XIX is dissolved in methanol, with the addition of the calculated amount of the particular acid the salt of which is the desired end product, and hydrogenated at ambient temperature under gentle pressure, e.g. up to 5 bar, until the uptake of hydrogen has ended.

The starting materials may be obtained from known compounds by conventional methods.

Thus, the starting materials for process 1 may be obtained from the corresponding nitriles by reacting them with HCl via the step of the imide chlorides or directly by reacting them with, for example, $C_{1-6}$-alcohols or benzyl alcohol in the presence of an acid such as HCl. The reaction of the nitrites with $H_2S$ in solvents such as pyridine or dimethylformamide in the presence of a base such as triethylamine and subsequent alkylation or benzylation result in compounds of formula X. Starting from carboxylic acid amides, which moreover correspond to the compounds of formula X, compounds of formula X may also be obtained by reaction with a trialkyloxonium salt such as triethyloxonium tetrafluoroborate, in a solvent such as dichloromethane, tetrahydrofuran or dioxane at temperatures between 0 and 50° C., preferably at ambient temperature.

The starting materials XIX may also be obtained by reacting corresponding amidoximes instead of amidine analogously to method 1 or 2; by analogous reaction of corresponding nitriles from which the starting materials XIX are finally obtained by the addition of hydroxylamine.

The compounds according to the invention are therapeutically useful, particularly in the light of their $LTB_4$-antagonistic activity. They are therefore suitable for use, particularly, in those diseases in which inflammatory and/or allergic processes are involved, such as asthma, ulcerative colitis, psoriasis and also for treating gastropathy induced by non-steroidal antiphlogistics. The new compounds may also be used in conjunction with other active substances, e.g. antiallergics, secretolytics, $\beta_2$-adrenergics, steroids for inhalation, antihistamines and/or PAF-antagonists. They may be administered by topical, oral, transdermal, nasal or parenteral route or by inhalation.

The therapeutic or prophylactic dose is dependent on the nature and gravity of the disease, as well as the potency of the individual compounds and the body weight of the patient. For oral administration the dose is between 10 and 250 mg, preferably between 20 and 200 mg. For inhalation, the patient takes between about 2 and 20 mg of active substance. The new compounds may be administered in conventional preparations such as plain or coated tablets, capsules, lozenges, powders, granules, solutions, emulsions, syrups, aerosols for inhalation, ointments and suppositories.

The Examples which follow illustrate some possible formulations for the preparations.

Formulation Examples

1. Tablets

| Composition: | |
|---|---|
| Active substance according to | |
| the invention | 20 parts by weight |
| Stearic acid | 6 parts by weight |
| Dextrose | 474 parts by weight |

The constituents are processed in the usual way to form tablets weighing 500 mg. If desired, the content of active substance may be increased or reduced and the quantity of dextrose reduced or increased accordingly.

2. Suppositories

| Composition: | |
|---|---|
| Active substance according to | |
| the invention | 100 parts by weight |
| Powdered lactose | 45 parts by weight |
| Cocoa butter | 1555 parts by weight |

The ingredients are processed in the usual way to form suppositories weighing 1.7 g.

3. Powder for inhalation

Micronised powdered active substance (compound of formula I; particle size about 0.5 to 7 µm) is packed into hard gelatine capsules in a quantity of 5 mg, optionally with the addition of micronised lactose. The powder is inhaled using conventional inhalation devices, e.g. according to DE-A 3 345 722.

The compounds according to the invention were tested inter alia for their activity in the tests described below.

a) U937—Receptor Binding Test/$LTB_4$

The binding of $^3H$-$LTB_4$ (3 nM) to vital U937 cells (differentiated human monocytary cell line with naturally expressed $LTB_4$ receptors) is inhibited, in dosage dependent manner, by an increasing concentration of the test substance (incubation 2 hours at 0° C.). After the unbound $^3H$-$LTB_4$ has been separated off by membrane filtration, the radioactivity of the bound $LTB_4$ receptor/$^3H$-$LTB_4$ complex is quantified by scintillation measurement. The affinity (inhibition constant $K_i$) was determined by repeated adaptation of a displacement curve to the measurements (program: "coupled mass equilibria" on Wang computer).

b) Aggregation of Neutrophilic Granulocytes in the Guinea-pig

Indicated by $LTB_4$ in vitro (increase in light transmission in the aggregometer, recorded in mm; each experiment repeated twice): inhibition 2 minutes after incubation with test substance in polydiol/DMSO.

c) Leukotrien-$B_4$-indicated Accumulation of Neutrophiles in the Mouse Ear

Evaluation of the neutrophilic influx by photometric measurement (mOD/min) of the myeloperoxidase activity (Bradley et al.: J. Invest. Dermatol. 78, 206, 1982) in the skin of the ear. Increase 6 hours after topical treatment of the left ear with $LTB_4$ (250 ng on each side) compared with the right ear (2×5 µl acetone as solvent).

Substance administered by oral route in 1% tylose 300, 30 minutes before the $LTB_4$ stimularion.

4. Results

| | a)* | b)** | c)*** |
|---|---|---|---|
| [structure: H3CO-phenyl-propyl-O-(CH2)4-O-phenyl-C(=NH)NH2] | 12,0 | 1,9 | 0,8 |
| [structure: RO-phenyl-propyl-O-(CH2)2-O-biphenyl-C(=NH)NH2] R = H | 3,8 | 0.06 | 1,2 |
| R = CH3 | 6,3 | 0,31 | 0,9 |
| [structure: RO-phenyl-propyl-O-(CH2)2-O-phenyl-C(=NH)NH2] R = H | 1,7 | 0,02 | 3,8 |
| R = CH3 | 15,0 | 0,32 | 2,3 |

*Receptor binding U937-8 $K_i$ [nM](1)
**$LTB_4$-induced neutroph. Aggr. $EC_{50}$ [μM](2)
****$LTB_4$-induced neutroph. Accum. p.o. $ED_{50}$ [mg/kg]

The $^3$H-$LTB_4$-receptor binding to guinea-pig spleen cells in the presence of 10% blood plasma yielded $K_i$-values of, in some cases, far less than 1 μM, more particularly between 0.2 and 0.02. Inhibition of the $LTB_4$-induced aggregation of neutrophiles resulted in $EC_{50}$-values between about 0.5 and 0.05 μM.

Particular mention should be made of the compounds according to Examples 1 and 5 and Nos. 10, 11, 13, 19, 20, 22 and 23 from Table I, No. 1 from Table II, No. 2 from Table III.

The Examples which follow illustrate the possible methods of preparing the compounds according to the invention.

Process 1

EXAMPLE 1

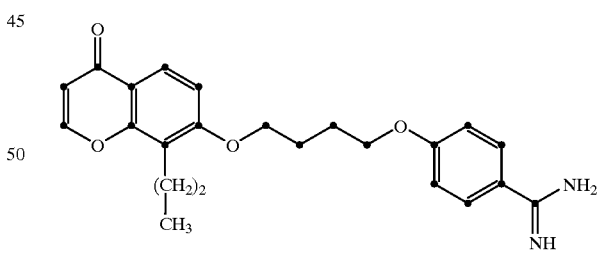

To a solution of 2.0 g of 7-[4-(4-cyano-phenoxy)-E-but (2)-enyloxy]-8-propyl-4H-1-benzopyran-4-one in 50 ml of chloroform and 1.5 ml of ethanol are added 5 ml of a solution of hydrogen chloride in diethylether (17%). The mixture is left to stand for 14 days at ambient temperature and the product is precipitated with diethylether. 1.15 g of 7-[4-(4-imidacarboxyethyl-phenoxy)-E-but (2)-enyloxy]-8-propyl-4H-1-benzopyran-4-one-hydrochloride are obtained. The imidoester is mixed with 50 ml of ethanolic ammonia solution (5 M) and heated for 3 hours to 70° C. The mixture is evaporated down and the residue is chromatographed (chloroform/methanol 7:3, silica gel). After recrystallisation from dichloromethane/diethylether, 0.6 g of 7-[4-(4-amidino-phenoxy)-E-but(2)-enyloxy]-8-propyl-4H-1-benzopyran-4-one-hydrochloride are obtained (m.p. 144–148° C.).

EXAMPLE 2

To a solution of 2.5 g of 4-[4-(2-propyl-3-methoxy-phenoxy)-butyloxyl-benzonitrile, prepared from 2-propyl-3-methoxy-phenol and 4-bromobutoxybenzonitrile, in 40 ml of ethanol, hydrogen chloride is introduced at −20° C. with stirring for 1 hour and the mixture is left to stand at ambient temperature for 16 hours.

The solvent is distilled off in vacuo and the residue is taken up in 50 ml of ethanol. A mixture of 14 ml of ethanolic ammonia solution and 50 ml of ethanol is added dropwise thereto and the mixture is left to stand for 24 hours at ambient temperature. The solvent is evaporated off and the residue is chromatographed (chloroform/methanol 8:2; silica gel 60). 1.8 g of 4-[4-(2-propyl-3-methoxy-phenoxy)-butyloxy]-benzamidine-hydrochloride-hemihydrate are obtained. (M.p. 117–121° C.).

EXAMPLE 3

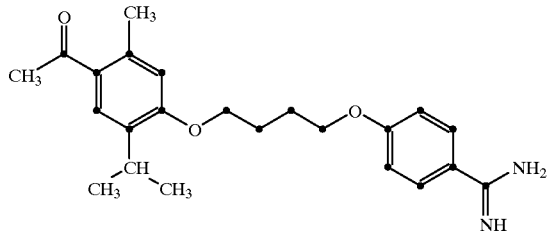

Hydrogen chloride is introduced at −20° C. into a solution of 32.0 g of 4-[(4-acetyl-2-isopropyl-5-methyl-phenoxy)-butyloxy]-benzonitrile in 350 ml of ethanol and the resulting mixture is stirred for 48 hours. The crystals precipitated are suction filtered and washed with diethylether. 41.0 g of 4-[4-(4-acetyl-2-isopropyl-5-methyl-phenoxy)-butyloxy]-benzimidoethylester-hydrochloride are obtained (m.p. 100–102° C. decomp.). 15.0 g of the imidoester are added at ambient temperature in several batches to 33 ml of ethanolic ammonia solution (5 M) and 100 ml of ethanol. The mixture is stirred for 36 hours at ambient temperature, evaporated down and the residue is stirred with 50 ml of water. The residue is suction filtered, recrystallised from 30 ml of ethanol and washed with diethylether. 11.5 g of 4-[4-(4-acetyl-2-isopropyl-5-methyl-phenoxy)-butyloxy]-benzamidine-hydrochloride are obtained (m.p. 182–183° C. decomp.).

EXAMPLE 4

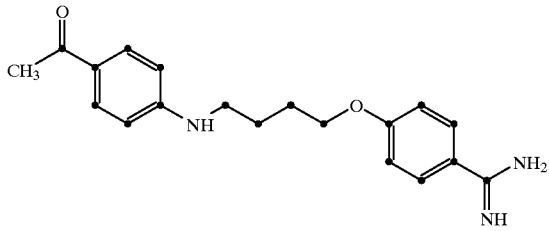

Hydrogen chloride is introduced at −20° C. into a solution of 3.0 g of 4-[4-(4-cyano-phenoxy)-butylamino]-acetophenone in 40 ml of ethanol, with stirring, for 4 hours and the mixture is left to stand at ambient temperature for 16 hours. The solvent is distilled off in vacuo and the residue is taken up in 50 ml of ethanol. A mixture of 14 ml of ethanolic ammonia solution and 50 ml of ethanol is added dropwise thereto and the mixture is left to stand for 24 hours at ambient temperature. The solvent is evaporated off and the residue is chromatographed (chloroform/methanol 7:3, silica gel 60). 0.3 g of 4-[4-(4-amidino-phenoxy) butylamino]-acetophenone are obtained (m.p. 200–202° C.).

Process 2

EXAMPLE 6

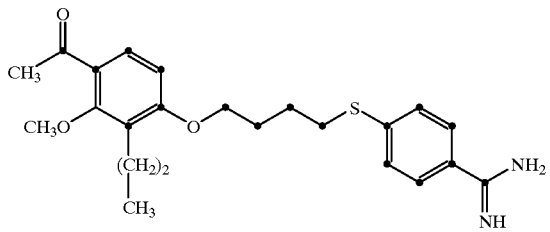

8.2 g of 4-acetyl-3-methoxy-2-propyl-phenol are dissolved in 80 ml of dimethylformamide and 1.1 g of sodium hydride is added in batches to the solution (as an 80% dispersion in white oil). The mixture is heated to 80° C. for 30 minutes and combined with a solution of 5.75 g of 4-(4-bromopropylthio)-benzamidine (prepared from dibromobutane and 4-cyanobenzothiol by means of 4-(4-bromobutyl-thio)-benzonitrile) in 40 ml of dimethylformamide. After 5 hours at 80° C. the mixture is allowed to cool, acidified with ethereal hydrochloric acid and the solvents are distilled off in vacuo. The residue is taken up in ethanol and filtered. The filtrate is concentrated by evaporation. The process is repeated with chloroform and acetonitrile. The residue is stirred with diethylether. After decanting, 5.65 g of a brownish-yellow oil are left. The product is chromatoqraphed (chloroform/methanol 7:3, silica gel). 2.4 g of an oil are obtained which is crystallised from toluene. The product is dissolved in acetonitrile, acidified with ethereal hydrochloric acid. The crystals are suction filtered, washed with cold acetonitrile, dissolved in water and crystallised once more after the addition of 2 N hydrochloric acid. 0.8 g of 4-[4-4-acetyl-3-methoxy-2-propylphenxy)-butylthio]-benzamidine-hydrochloride are obtained (m.p. 120–122° C.).

Process 3

EXAMPLE 7 a) 4-[4-(4-Acetylphenoxy-butoxy]-benzamidoxime 45.6 g (0.3 mol) of 4-hydroxybenzamidoxime and 81.3 g (0.3 mol) of 4-bromo-butoxy-acetophenone are dissolved in 300 ml of dimethylformamide. After the addition of 55.2 g (0.4 mol) of anhydrous potassium carbonate the mixture is heated to 80° C. for 2 hours. The inorganic salts are suction filtered, evaporated down in vacuo and recrystallised from acetonitrile.

Yield: 47.8 g

M.p.: 164.5–165.5° C.

b) 3-[4-(4-Acetylphenoxy)butoxy]-benzamidine-methanesulphonate 47.8 g of the compound synthesised according to a) are dissolved in 10 times the quantity of methanol with the addition of the calculated amount of methanesulphonic acid. After the addition of Raney nickel, the mixture is hydrogenated at 5 bar until the uptake of hydrogen has ended. The mixture is suction filtered, the solvent is distilled off in vacuo and the residue is recrystallised from ethanol.

Yield: 45.2 g

M.p.: 204–204.5° C.

The other compounds of formula I can be obtained according to the processes described above. "Ac" hereinafter denotes $CH_3CO-$.

TABLE I

Compounds of formula (Ia)

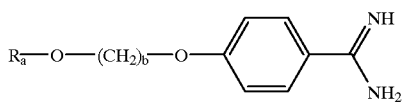

| No. | $R_a$ | b | M.p.[° C.] (Hydrochloride) |
|---|---|---|---|
| 1 | Ac—[naphthalene]— | 2 | 240 |
| 2 | Ac—[phenyl with OCH₃, n-C₃H₇]— | 2 | 209–10 |
| 3 | CH₃O—[phenyl]— | 4 | — |
| 4 | Ac—[phenyl with CH₃, OCH₃]— | 4 | 143 |
| 5 | Ac—[phenyl with CH₃, CH₃, OCH₃]— | 4 | 124 |
| 6 | [biphenyl]— | 4 | 190 |
| 7 | [methylnaphthalene]— | 4 | 199–4 |
| 8 | Ac—[phenyl with OH]— | 4 | 189 |
| 9 | CH₃O—[phenyl]— | 4 | 125–31 |
| 10 | [benzophenone]— | 4 | 148–50 |
| 11 | [phenyl-Ac]— | 4 | 132–40 |
| 12 | Ac—[phenyl]— | 4 | 160–3 |
| 13 | [chromanone with n-C₃H₇]— | 4 | 160–5 |
| 14 | [naphthalene with Ac]— | 4 | 228–31 |

TABLE I-continued
Compounds of formula (Ia)
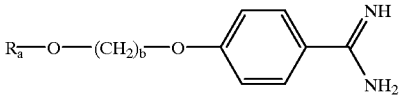
| No. | $R_a$ | b | M.p.[° C.] (Hydrochloride) |
|---|---|---|---|
| 15 | 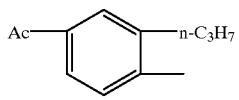 | 4 | 140–6 |
| 16 | 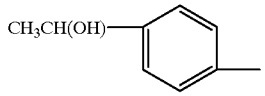 | 4 | |
| 17 | 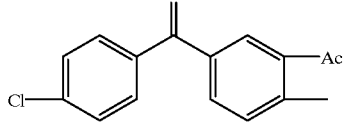 | 4 | 170–2 |
| 18 | 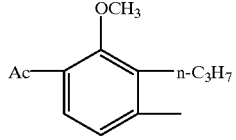 | 4 | 149–50 |
| 19 | 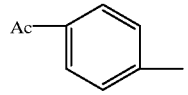 | 4 | 167 (decomp.) |
| 20 | 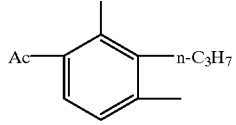 | 4 | 179 |
| 21 | 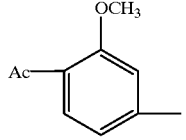 | 4 | 168–70 (decomp.) |
| 22 | 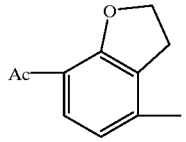 | 4 | 187 (decomp.) |
| 23 | 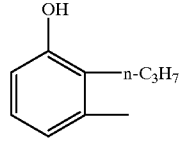 | 4 | 166–8 |
| 24 | 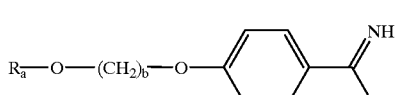 | 4 | |
| 25 | 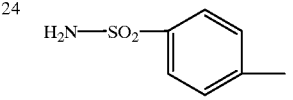 | 4 | |
| 26 | 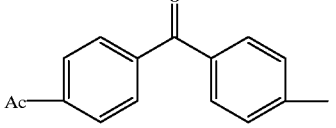 | 4 | |
| 27 | 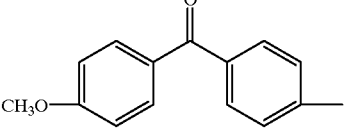 | 4 | |
| 28 | 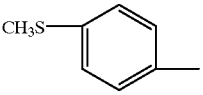 | 4 | |
| 29 | 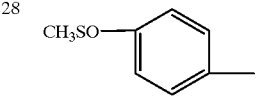 | 4 | 174–5 |
| 30 | 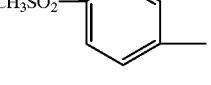 | 4 | 155–60 |
| 31 | 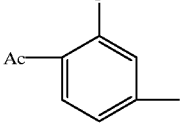 | 4 | 194–60 |

TABLE I-continued

Compounds of formula (Ia)

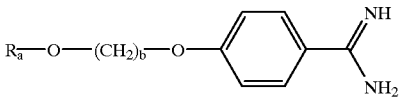

| No. | Ra | b | M.p.[° C.] (Hydrochloride) |
|---|---|---|---|
| 32 | 3-hydroxyphenyl | 4 | 214–23 |
| 33 | 4-(CF$_3$O)phenyl | 4 | |
| 34 | 4-((CH$_3$)$_3$CO)phenyl | 4 | |
| 35 | 4-(4-chlorobenzoyl)phenyl | 4 | 145–8 |
| 36 | 2-(n-C$_3$H$_7$)phenyl | 4 | 128–31 |
| 37 | 2-(OCH$_3$)phenyl | 4 | |
| 38 | 4-Ac-3-OCH$_3$-phenyl | 4 | |
| 39 | 4-(C$_2$H$_5$CO)-3-OCH$_3$-phenyl | 4 | |
| 40 | 2-naphthyl | 4 | 194 |
| 41 | 4-Ac-phenyl | 6 | 132 |
| 42 | 4-CH$_3$-phenyl-CO-phenyl-4-Ac | 4 | |
| 43 | 4-CH$_3$-phenyl | 4 | |
| 44 | 2-OCH$_3$-phenyl | 4 | |

TABLE II

Compounds of formula (IIb)

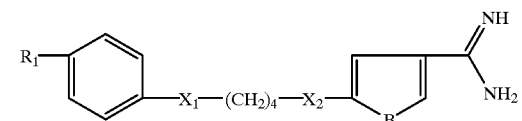

| No. | B | R$_1$ | X$_1$ | X$_2$ | M.p. [° C.] (Hydrochloride) |
|---|---|---|---|---|---|
| 1 | CH=CH | Ac | O | S | |
| 2 | CH=CH | Ac | O | SO | |
| 3 | CH=CH | Ac | O | SO$_2$ | 160–2 (Base) |
| 4 | CH=CH | Ac | S | S | |
| 5 | N=CH | Ac | O | S | 152–60 |
| 6 | CH=CH | Ac | O | NH | 200–2 |
| 7 | CH=CH | Ac | S | O | 196–7 |
| 8 | CH=CH | Ac | SO | O | |
| 9 | CH=CH | Ac | SO$_2$ | O | 208 |

TABLE III

Compounds of formula (Ic)

Ac—⟨C6H4⟩—X'₁—A'—X'₂—⟨C6H4⟩—C(=NH)NH₂

| No. | A' | X'₁ | X'₂ | M.p. [° C.] (Hydrochloride) |
|---|---|---|---|---|
| 1 | CH₂—CH=CH—CH₂ | O | O | 215–8 |
| 2 | o-xylylene (H₂C—C₆H₄—CH₂, ortho) | O | O | 196–202 |
| 3 | CH₂—CH(OH)—CH₂ | O | O | 205–9 |
| 4 | m-xylylene (H₂C—C₆H₄—CH₂, meta) | O | O | 183 |

TABLE IV

Compounds of formula (Id)

Ac—⟨C6H3(R₁)(R₂)⟩—O—(CH₂)₄—O—⟨C6H4(R₄)⟩—R_b

| No. | R_b | R₁ | R₂ | R₄ | M.p. [° C.] (Hydrochloride) |
|---|---|---|---|---|---|
| 1 | 2-C(=NH)NH₂ | H | H | H |  |
| 2 | 3-C(=NH)NH₂ | H | H | H | 174–6 |
| 3 | 4-C(=NH)NH₂ | n-C₃H₇ | OCH₃ | 2-OCH₃ | 124–7 |

TABLE IV-continued

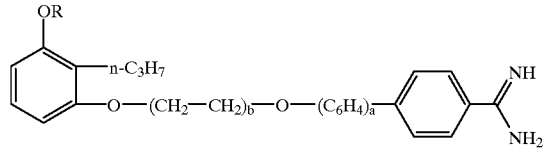

| No. | R | a | b | M.p. [° C.] |
|---|---|---|---|---|
| 1 | H | 0 | 1 | 178–80 (Hydrochloride) |
| 2 | H | 1 | 1 | 248–51 (Hydrochloride) |
| 3 | H | 1 | 2 |  |
| 4 | CH₃ | 0 | 1 | 176–8 (Hydrochloride) |
| 5 | CH₃ | 1 | 1 | 236–40 (Methanesulphonate) |
| 6 | C₂H₅ | 0 | 1 |  |
| 7 | C₂H₅ | 0 | 2 |  |
| 8 | n-C₃H₇ | 0 | 2 |  |
| 9 | n-C₃H₇ | 1 | 1 |  |
| 10 | i-C₃H₇ | 1 | 1 |  |
| 11 | n-C₄H₉ | 0 | 1 | 144–7 (Hydrochloride) |
| 12 | n-C₄H₉ | 0 | 2 |  |

We claim:

1. A compound of formula $$\text{(structure shown)}$$

wherein a is 0 or 1, b is 1 or 2,

R is $C_{1-4}$-alkyl, and if a=0 or 1 and b=1 and if a=1 and b=2, R may also be hydrogen, or the free base or physiolocgically acceptable acid addition salt thereof.

2. The compound as recited in claim 1, wherein a=0 or 1 and b=1 or a=0 and b=2.

3. The compound as recited in claim 2 wherein R is H, $CH_3$ or $C_2H_5$, a is 0 or 1 and b is 1.

4. The compound as recited in claim 2, wherein a is 0, b is 2 and R is $CH_3$.

5. A pharmaceutical composition of matter comprising a compound as recited in claim 1 and a pharmaceutically acceptable carrier.

6. A method for treating inflammatory or allergic process disease in a warm-blooded animal which comprises administering to said animal a therapeutically effective amount of a compound as recited in claim 1.

* * * * *